United States Patent
Hwang

(10) Patent No.: US 10,438,375 B2
(45) Date of Patent: Oct. 8, 2019

(54) WSI STREAMING METHOD

(71) Applicant: Infinitt Healthcare Co., Ltd., Seoul (KR)

(72) Inventor: Man Won Hwang, Incheon (KR)

(73) Assignee: Infinitt Healthcare Co., Ltd., Seoul (KR)

( * ) Notice: Subject to any disclaimer, the term of this patent is extended or adjusted under 35 U.S.C. 154(b) by 93 days.

(21) Appl. No.: 15/685,675

(22) Filed: Aug. 24, 2017

(65) Prior Publication Data

US 2019/0051018 A1 Feb. 14, 2019

(30) Foreign Application Priority Data

Aug. 11, 2017 (KR) .................. 10-2017-0102076

(51) Int. Cl.
| | | |
|---|---|---|
| G06K 9/00 | (2006.01) |
| G06T 9/40 | (2006.01) |
| G06T 1/00 | (2006.01) |
| G01N 33/52 | (2006.01) |
| H04N 21/232 | (2011.01) |
| H04N 21/2343 | (2011.01) |
| H04N 21/81 | (2011.01) |
| H04N 19/17 | (2014.01) |

(52) U.S. Cl.
CPC ............ *G06T 9/40* (2013.01); *G01N 33/52* (2013.01); *G06T 1/0007* (2013.01); *H04N 21/232* (2013.01); *H04N 21/23439* (2013.01); *H04N 21/8153* (2013.01); *H04N 19/17* (2014.11)

(58) Field of Classification Search
CPC ......... A61B 5/7232; A61B 5/725; A61B 5/00; G06T 7/0012; G06T 7/00; G06T 2207/20144; G06T 9/40; G06K 9/4604; G06K 9/46; G06K 9/6277; G06K 9/6269; H04N 19/176; G06F 19/321; G01N 29/07; G01N 33/52

See application file for complete search history.

(56) References Cited

U.S. PATENT DOCUMENTS

| | | | | |
|---|---|---|---|---|
| 8,611,620 | B2* | 12/2013 | Karasikov | G06K 9/00127 128/922 |
| 9,962,125 | B2* | 5/2018 | Hwang | A61B 5/7232 |
| 2003/0227673 | A1* | 12/2003 | Nakagawa | G02B 21/241 359/380 |
| 2012/0002852 | A1* | 1/2012 | Karasikov | G06K 9/00127 382/128 |

(Continued)

FOREIGN PATENT DOCUMENTS

KR 10-2011-0072098 A 6/2011

*Primary Examiner* — Amir Alavi
(74) *Attorney, Agent, or Firm* — Novick, Kim & Lee, PLLC; Sang Ho Lee

(57) ABSTRACT

Provided is a method in which a web client receives a whole slide image (WSI) having an image compression format and a tile size different depending on a digital pathology vendor from a digital pathology server in a streaming manner. The method includes a WSI acquisition operation of acquiring the WSI from the digital pathology server. The WSI acquisition operation includes a normalized tile definition operation of defining a normalized tile having a minimized time cost, a determination operation of comparing a tile with the normalized tile, and a conversion operation of optimizing the tile with the normalized tile.

9 Claims, 4 Drawing Sheets

(56) References Cited

U.S. PATENT DOCUMENTS

| | | | |
|---|---|---|---|
| 2013/0269441 A1* | 10/2013 | Doyle | G01N 29/07 |
| | | | 73/598 |
| 2014/0293117 A1* | 10/2014 | Murakami | G02B 21/365 |
| | | | 348/349 |
| 2017/0362656 A1* | 12/2017 | Umansky | C12Q 1/6883 |
| 2018/0089496 A1* | 3/2018 | Molin | G06K 9/0014 |
| 2018/0322631 A1* | 11/2018 | Madabhushi | G06T 7/0012 |

* cited by examiner

WSI STREAMING METHOD

CROSS-REFERENCE TO RELATED APPLICATION

This application claims priority to and the benefit of Korean Patent Application No. 10-2017-0102076, filed on Aug. 11, 2017, the disclosure of which is incorporated herein by reference in its entirety.

BACKGROUND

1. Field

The present invention relates to a whole slide image (WSI) streaming method, and more particularly, to a WSI streaming method that, because it is difficult to achieve consistent performance in a web environment during WSI image streaming due to various image compression formats and tile sizes depending on digital pathology scanner vendors, reduces performance deterioration depending on the vendors via tile image normalization through conversion during image acquisition and performs the tile image normalization by using a tile having a minimized time cost.

2. Discussion of Related Art

Digital pathology is an image-based information environment which is enabled by computer technology that allows for management of information generated in a digital slide. Digital pathology is enabled in part by virtual microscopy, which is the practice of producing an image with a microscope and delivering the produced image to a computer network.

Recently, digital pathology has been globally recognized as an emerging field of diagnostic medicine. As in the above, digital pathology has been getting the spotlight as an emerging field of diagnostic medicine. However, research and development of digital pathology are still in an early stage. The current stage of the research and development can be seen in the following circumstance. In Korea, there has been little research and development on a digital pathology system, and also there is no product associated with the research and development. Even in foreign countries, there are no digital pathology systems that have been approved for primary diagnosis by the U.S. Food and Drug Administration (FDA).

The present applicant thought there was a problem in that image opening speeds or image search speeds are very different depending on vendors when the applicant opened and viewed digital slide images (whole slide images (WSIs)), that is, WSI images of various vendors in a digital pathology system. In this field, there has been no opinion on the matter.

Also, there is another problem in that an image loading speed is slow when opening or searching for an image through a web client because a server performs conversion on images in most cases. Also, when JPIP is used, there is another problem in that the image loading speed is reduced because a browser of a web client cannot directly support j2k, and thus the web browser should perform j2k decoding with JavaScript.

SUMMARY

The present invention is designed to solve the above problems, and is directed to providing a whole slide image (WSI) streaming method that, because it is difficult to achieve consistent performance in a web environment during WSI image streaming due to various image compression formats and tile sizes depending on digital pathology scanner vendors, reduces performance deterioration depending on the vendors via tile image normalization through conversion during image acquisition and performs the tile image normalization by using a tile having a minimized time cost. Furthermore, the present invention is also directed to providing a WSI streaming method capable of improving a response and a time cost through caching on the basis of a region and access frequency when tile data is repeatedly and frequently requested.

According to an aspect of the present disclosure, there is provided a method in which a web client receives a WSI having a different image compression format and a different tile size depending on a digital pathology scanner vendor from a digital pathology server in a streaming manner, the method including a WSI acquisition operation of acquiring the WSI from the digital pathology server, wherein the WSI acquisition operation comprises: a normalized tile definition operation of defining a normalized tile having a minimized time cost at a navigation level including a thumbnail level, wherein the time cost is a time required to view the same region, and defining a normalized tile having a minimized time cost at a base level; a comparison determination operation of determining that a base level tile of the WSI and a navigation level tile of the WSI do not need to be optimized with the normalized tiles (Case 1), that only the navigation level tile needs to be optimized with the normalized tile while the base level tile is used as it is (Case 2), or that both the base level tile and the navigation level tile need to be optimized with the normalized tiles (Case 3); and a conversion operation of preventing optimization of both the base level tile of the WSI and the navigation level tile of the WSI with the normalized tiles in Case 1, optimizing only the navigation level tile with the normalized tile while using the base level tile as it is in Case 2, and optimizing the base level tile and the navigation level tile with the normalized tiles in Case 3.

The time cost may be proportional to (basic service response time+tile load time+tile transfer time)×(number of tiles).

The method may further include an operation of transcoding the acquired WSI into a JPEG, searching for and loading a block, performing a JPEG image block transfer, performing JPEG decoding, and updating and displaying the block after the WSI acquisition operation.

The block may indicate the normalized tile.

The web client may include a first region cache buffer, and the digital pathology server may include a second region cache buffer and a raw cache buffer. The method may include buffering, by the first region cache buffer, information regarding tiles adjacent to a viewed region, which is a region viewed by a user of the web client; buffering, by the second region cache buffer, the information regarding the tiles adjacent to the viewed region, which is the region viewed by the user of the web client; and buffering, by the raw cache buffer, the tiles in descending order of hit rate on the basis of the hit rate.

The method may further include performing, by the first region cache buffer, background loading from the second region cache buffer.

The hit rate may be calculated on the basis of a tile read request frequency, a total recent access time, and information regarding how often a corresponding tile has recently been requested per unit time.

When the raw cache buffer buffers the same tile information as the second region cache buffer, the raw cache buffer may store only an index of the second region cache buffer having the information instead of storing the information.

The method may further include calculating, by the web client, a minimum level for down-sampling at a current view size; generating, by the web client, a list of all tiles overlapping the viewed region on the basis of the minimum level and requesting an $i^{th}$ tile image in the tile list from the digital pathology server; and returning, by the digital pathology server, the $i^{th}$ tile image to the web client, wherein i is a natural number ranging from 1 to n, which is the number of tiles.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
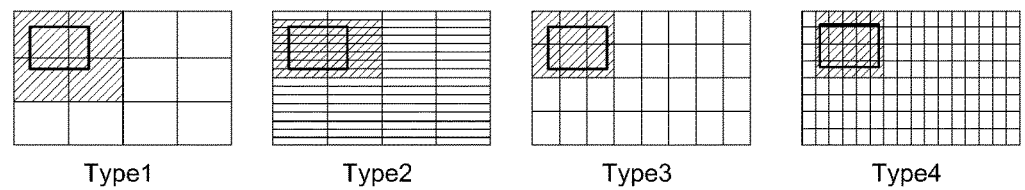
FIG. 1 is a diagram showing types of whole slide images (WSIs)

Hereinafter, example embodiments of the present invention will be described below in more detail with reference to the accompanying drawings. Terms and words used in the specification and the claims are not to be interpreted as being limited to commonly-used dictionary meanings, but should be interpreted as being relevant to the technical scope of the invention based on the fact that the inventor may properly define the concept of the terms to explain the invention in the best ways.

Therefore, the embodiments and the configurations depicted in the drawings are for illustrative purposes only and are not intended to represent the entire technical scope of the embodiments, so it should be understood that various equivalents and modifications may exist at the time of filing this application.

FIG. 1 is a diagram showing types of whole slide images (WSIs). It can be seen in Table 1 that times needed to view the same regions are different depending on a type of WSI provided by a vendor. The term "time required to view the same region" used herein will be referred to as the term "time cost." That is, the time cost is proportional to (basic service response time+tile load time+tile transfer time)× (number of tiles).

TABLE 1

| Category | Tile Size (KB) | Basic Service Response Time (ms) | Tile Load Time (ms) | Tile Transfer Time (ms) | View Tile Time (ms) | View Region Time (ms) |
| --- | --- | --- | --- | --- | --- | --- |
| Type1 | 100 | 2 | 20 | 20 | 42 | 42 × 4 = 168 |
| Type2 | 40 | 2 | 15 | 10 | 27 | 27 × 7 = 189 |
| Type3 | 30 | 2 | 14 | 9 | 25 | 25 × 6 = 150 |
| Type4 | 15 | 2 | 12 | 5 | 19 | 19 × 20 = 380 |

Such a problem has never been recognized in this field, and the present applicant considered a type of WSI to be an optimal type in terms of time cost. Furthermore, because vendors have various image compression formats and tile sizes, it is difficult to achieve consistent performance in a web environment during WSI image streaming, and so the present applicant reduced performance deterioration depending on vendors by normalizing tile images through conversion during image acquisition.

Figure 2:
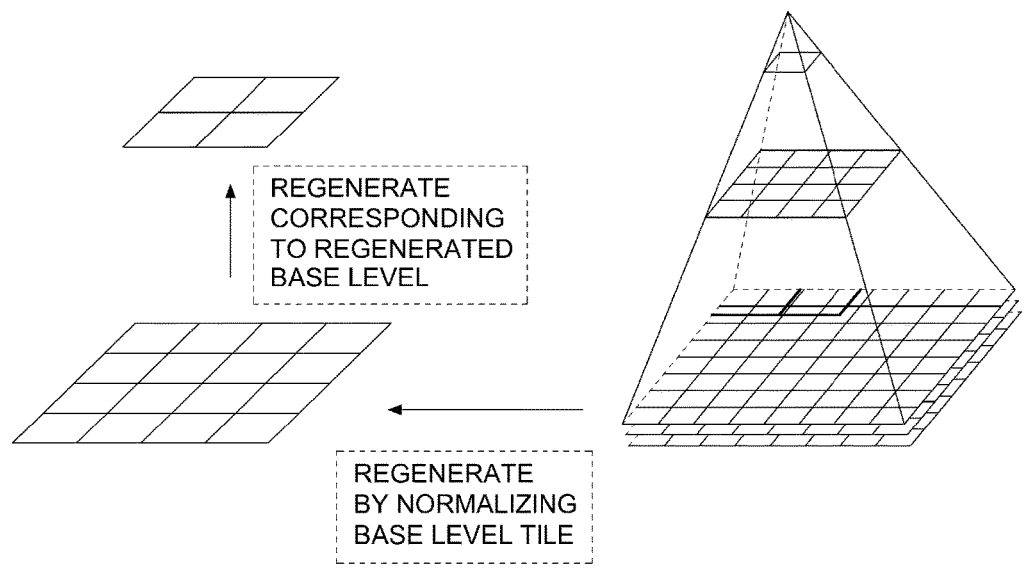
FIG. 2 is a diagram showing a case in which a tile specification and an image format need to be optimized.

FIG. 2 is a diagram showing a case in which a tile specification and an image format need to be optimized.

In FIG. 2, it can be seen that a base level tile is normalized and regenerated using a tile having a minimized time cost and a navigation level tile is regenerated corresponding to the regenerated base level tile.

Figure 3:
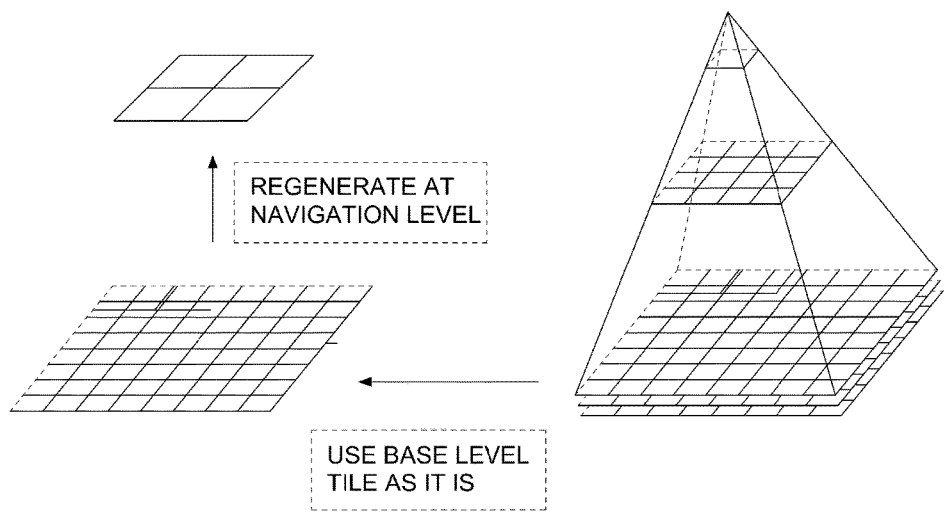
FIG. 3 is a diagram showing a case in which only a navigation layer needs to be optimized.

FIG. 3 is a diagram showing a case in which only a navigation layer needs to be optimized. In FIG. 3, it can be seen that only a navigation level tile is regenerated while a base level tile is used as it is.

Figure 4:
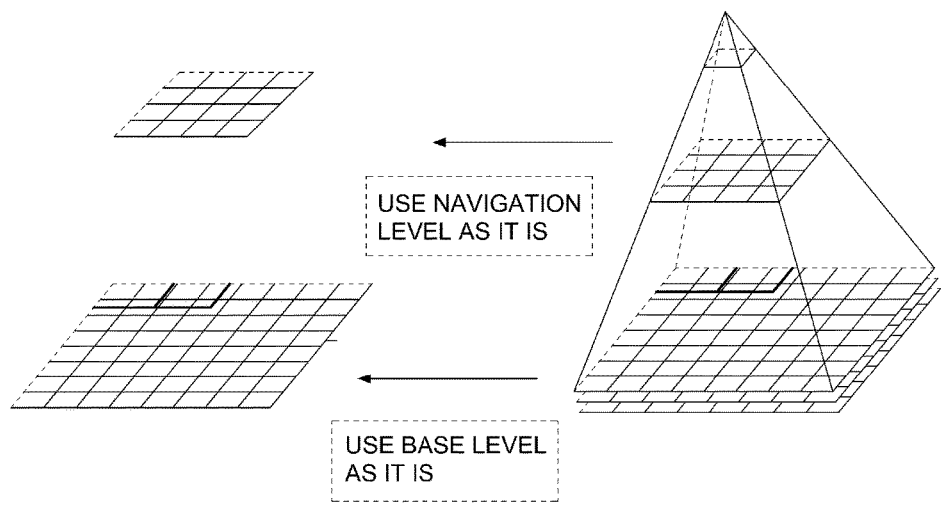
FIG. 4 is a diagram showing a case in which both a base level tile and a navigation level tile do not need to be optimized.

FIG. 4 is a diagram showing a case in which both a base level tile and a navigation level tile do not need to be optimized. It can be seen that a base level tile and a navigation level tile are used as they are.

As shown in FIGS. 2 to 4, the WSI streaming method according to the present invention includes setting a normalized tile having a minimized time cost at a base level and a navigation level (including a thumbnail level), comparing a base level tile or a navigation level tile with the normalized tile when there are various image compression formats and tile sizes depending on digital pathology vendors, determining that both the base level tile and the navigation level tile do not need to be optimized (see FIG. 4), that only the navigation level tile needs to be optimized (normalized) while the base level tile is used as it is (see FIG. 3), and that both the base level tile and the navigation level tile need to be optimized or normalized (see FIG. 2) depending on cases, as shown in FIGS. 2 to 4, and performing conversion into the normalized tile having the minimized time cost at the base level and navigation level (including the thumbnail level) according to the cases.

Figure 5:
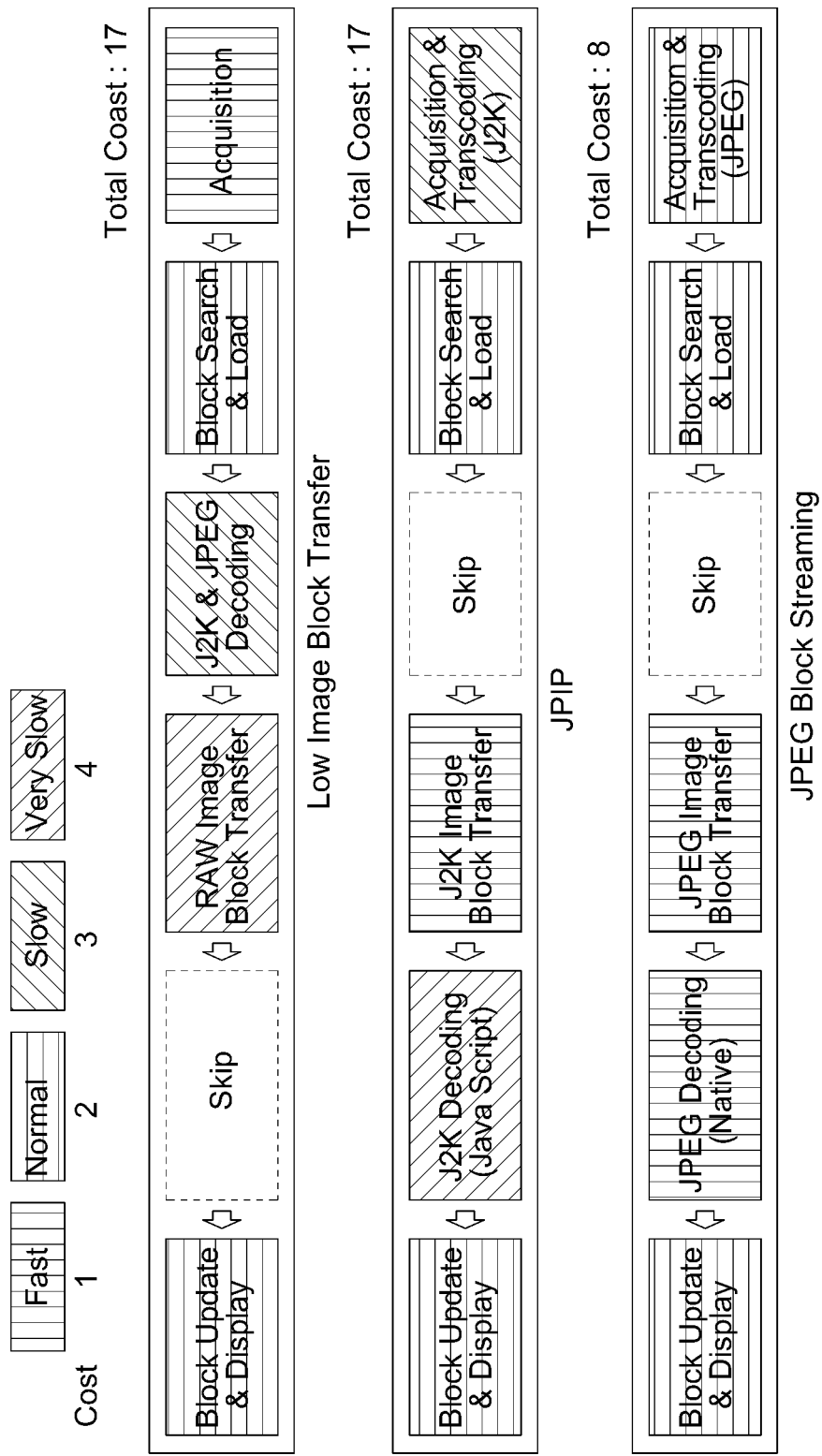
FIG. 5 is a diagram showing that time costs are different depending on image compression formats.

FIG. 5 is a diagram showing that time costs are different depending on image compression formats.

As shown in FIG. 5, after the image acquisition step described with reference to FIGS. 1 to 4, a step of transcoding the image into JPEG, searching for and loading a block, performing a JPEG image block transfer, performing JPEG decoding, and updating and displaying the block is performed. Also, when JPIP is used, a processing speed is reduced because a browser of a web client cannot directly support j2k and thus the web browser should perform j2k decoding with JavaScript. Here, the block denotes the normalized tile described with reference to FIGS. 1 to 4.

Figure 6:
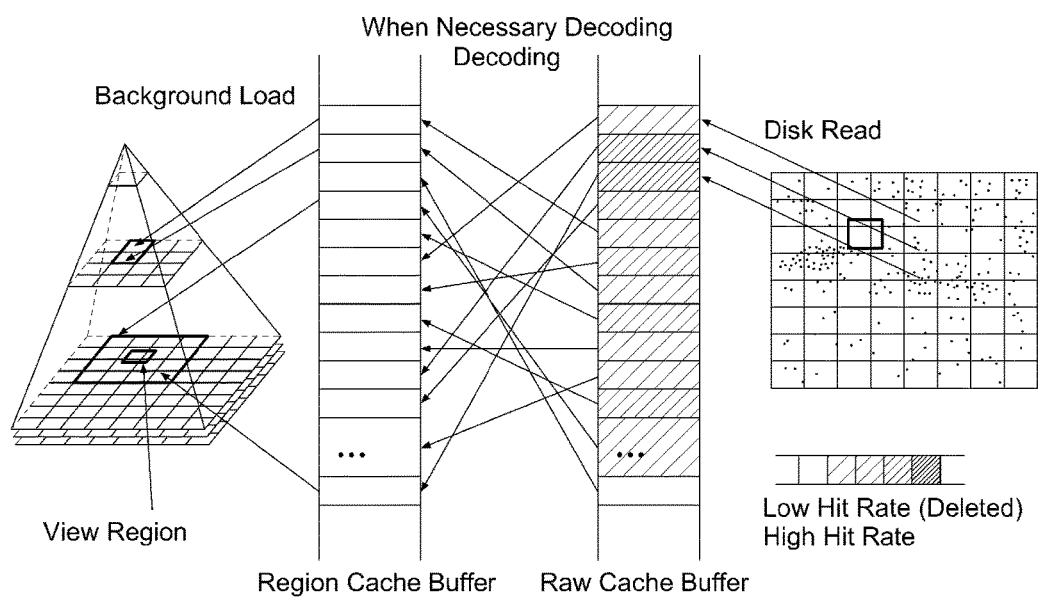
FIG. 6 is a diagram illustrating caching in a WSI streaming method according to the present invention.

FIG. 6 is a diagram illustrating caching in a WSI streaming method according to the present invention. A region cache buffer of FIG. 6 may be located in a web client and/or a digital pathology server, and a raw cache buffer may be located in the digital pathology server. In an optimal case, a first region cache buffer is located in the web client, a second region cache buffer is located in the digital pathology server, and the raw cache buffer is located in the digital pathology server.

In the web client, the first region cache buffer buffers information regarding tiles adjacent to a viewed region, which is a region currently being viewed by a user. In the digital pathology server, the second region cache buffer buffers the information regarding the tiles adjacent to the viewed region, which is the region currently being viewed by the user. It is possible to reduce a time cost by the first region cache buffer loading the information stored in the second region cache buffer in the background.

Tiles are buffered in the raw cache buffer of the digital pathology server in descending order of a hit rate, which uses a request frequency, a recent access time, and information regarding how often a request has recently been made per unit time, on the basis of the hit rate, and tiles exceeding a capacity of the raw cache buffer are deleted from the raw cache buffer. When the raw cache buffer buffers the same tile information as the second region cache buffer, the raw cache buffer may store only an index of the second region cache buffer having the information instead of storing the information.

During JPEG block streaming, image quality control is performed for high response. Among a WSI, a thumbnail image is loaded first, a subsequent level block is transmitted and loaded, and then a base level block is transmitted and loaded when necessary.

Also, the web client calculates a minimum level for down-sampling at a current view size. The web client generates a list of all tiles overlapping the viewed region on the basis of the minimum level and requests an $i^{th}$ tile image from the tile list. The digital pathology server returns the $i^{th}$ tile image. Here, i is a natural number in the range of 1 to n, and n is the number of tiles in the tile list.

According to the WSI streaming method according to the present invention, first, because it is difficult to achieve consistent performance in a web environment during WSI image streaming due to various image compression formats and tile sizes depending on digital pathology scanner vendors, it is possible to reduce performance deterioration depending on the vendors via tile image normalization through conversion during image acquisition and perform the tile image normalization by using a tile having a minimized time cost.

Second, it is also possible to improve a response and a time cost through caching on the basis of a region and access frequency when tile data is repeatedly and frequently requested.

While the present invention has been described with reference to limited embodiments and drawings, the present invention is not limited thereto. It will be appreciated that various modifications and changes can be made by those skilled in the art without departing from the scope and equivalents of the appended claims.

What is claimed is:

1. A method in which a web client receives a whole slide image (WSI) having a different image compression format and a different tile size depending on a digital pathology scanner vendor from a digital pathology server in a streaming manner, the method comprising a WSI acquisition operation of acquiring the WSI from the digital pathology server, wherein the WSI acquisition operation comprises:
   defining a normalized tile having a minimized time cost at a navigation level including a thumbnail level, wherein the time cost is a time required to view the same region, and defining a normalized tile having a minimized time cost at a base level;
   determining whether a base level tile of the WSI and a navigation level tile of the WSI do not need to be optimized with the normalized tiles (Case 1), whether only the navigation level tile needs to be optimized with the normalized tile while the base level tile is used as it is (Case 2), or whether both the base level tile and the navigation level tile need to be optimized with the normalized tiles (Case 3); and
   preventing optimization of both the base level tile of the WSI and the navigation level tile of the WSI with the normalized tiles in Case 1, optimizing only the navigation level tile with the normalized tile while using the base level tile as it is in Case 2, and optimizing the base level tile and the navigation level tile with the normalized tiles in Case 3.

2. The method of claim 1, wherein the time cost is proportional to (basic service response time+tile load time+ tile transfer time)×(number of tiles).

3. The method of claim 2, further comprising an operation of transcoding the acquired WSI into a JPEG, searching for and loading a block, performing a JPEG image block transfer, performing JPEG decoding, and updating and displaying the block after the WSI acquisition operation.

4. The method of claim 3, wherein the block indicates the normalized tile.

5. The method of claim 4, wherein:
   the web client includes a first region cache buffer, and the digital pathology server includes a second region cache buffer and a raw cache buffer; and
   the method further comprises:
      buffering, by the first region cache buffer, information regarding tiles adjacent to a viewed region, which is a region viewed by a user of the web client;
      buffering, by the second region cache buffer, the information regarding the tiles adjacent to the viewed region, which is the region viewed by the user of the web client; and
      buffering, by the raw cache buffer, the tiles in descending order of a hit rate on the basis of the hit rate.

6. The method of claim 5, further comprising performing, by the first region cache buffer, background loading from the second region cache buffer.

7. The method of claim 6, wherein the hit rate is calculated on the basis of a tile read request frequency, a total recent access time, and information regarding how often a corresponding tile has recently been requested per unit time.

8. The method of claim 7, wherein when the raw cache buffer buffers the same tile information as the second region cache buffer, the raw cache buffer stores only an index of the second region cache buffer having the information instead of storing the information.

9. The method of claim 8, further comprising:
calculating, by the web client, a minimum level for down-sampling at a current view size;
generating a list of all tiles overlapping the viewed region on the basis of the minimum level and requesting an $i^{th}$ tile image in the tile list from the digital pathology server, by the web client; and
returning, by the digital pathology server, the $i^{th}$ tile image to the web client, wherein
i is a natural number ranging from 1 to n (here, n is the number of tiles).

* * * * *